US007867393B2

(12) United States Patent
Duchamp et al.

(10) Patent No.: US 7,867,393 B2
(45) Date of Patent: *Jan. 11, 2011

(54) INTEGRATED MODULE FOR BLOOD TREATMENT

(75) Inventors: Jacques Duchamp, Bron (FR); Aziz Aberkane, Decines (FR); Gabriel Meyssonnier, Dizimieu (FR); Dominique Pouchoulin, Tramoyes (FR)

(73) Assignee: Gambro Lundia AB (SE)

( * ) Notice: Subject to any disclaimer, the term of this patent is extended or adjusted under 35 U.S.C. 154(b) by 687 days.

This patent is subject to a terminal disclaimer.

(21) Appl. No.: 11/785,004

(22) Filed: Apr. 13, 2007

(65) Prior Publication Data

US 2007/0193940 A1  Aug. 23, 2007

Related U.S. Application Data

(62) Division of application No. 10/771,536, filed on Feb. 5, 2004, now Pat. No. 7,223,338.

(60) Provisional application No. 60/470,451, filed on May 15, 2003.

(30) Foreign Application Priority Data

Feb. 7, 2003  (IT)  .......................... MI2003A0214

(51) Int. Cl.
  *B01D 61/30*  (2006.01)
  *B01D 61/28*  (2006.01)
  *B01D 63/00*  (2006.01)

(52) U.S. Cl. .................... 210/232; 210/195.2; 210/240; 210/258; 210/321.6; 137/861; 248/274.1; 248/295.11; 248/309.1; 248/560; 248/576; 312/209; 604/4.01; 604/6.09; 604/6.11

(58) Field of Classification Search .............. 210/195.2, 210/232, 239, 240, 249, 258, 321.6, 416.1; 604/4.01, 6.09, 6.11; 137/111, 269, 861; 138/111, 115, 118; 284/274.1, 295.11, 309.1, 284/560, 576; 312/209
See application file for complete search history.

(56) References Cited

U.S. PATENT DOCUMENTS 3,909,045 A  9/1975  Meagher
4,009,107 A  2/1977  Miller et al.
4,263,808 A  4/1981  Bellotti et al.

(Continued)

FOREIGN PATENT DOCUMENTS

AU  744404  1/1999

(Continued)

OTHER PUBLICATIONS

International Search Report for International Application No. PCT/IB2004/000055.

*Primary Examiner*—John Kim
(74) *Attorney, Agent, or Firm*—Finnegan, Henderson, Farabow, Garrett & Dunner, LLP

(57) ABSTRACT

The support element (4) is provided with a plurality of connectors (7), (8), (11) which receive corresponding counter-connectors of a blood treatment device. The support element is also predisposed to include a fluid distribution circuitry cooperating with the blood treatment device in order to provide an integrated module for blood treatment. An assembly process of the integrated module for blood treatment is also described.

30 Claims, 9 Drawing Sheets

U.S. PATENT DOCUMENTS

| | | | |
|---|---|---|---|
| 4,379,452 A | 4/1983 | DeVries |
| 4,424,009 A | 1/1984 | van Os |
| 4,436,620 A | 3/1984 | Bellotti et al. |
| 4,526,515 A | 7/1985 | DeVries |
| 4,637,813 A | 1/1987 | DeVries |
| 4,844,810 A | 7/1989 | Richalley et al. |
| 4,871,012 A | 10/1989 | Kuo |
| 4,886,431 A | 12/1989 | Soderquist et al. |
| 4,950,245 A | 8/1990 | Brown et al. |
| 5,311,908 A | 5/1994 | Barone et al. |
| 5,427,509 A | 6/1995 | Chapman et al. |
| 5,443,451 A | 8/1995 | Chapman et al. |
| 5,462,416 A | 10/1995 | Dennehey et al. |
| 5,482,440 A | 1/1996 | Dennehey et al. |
| 5,641,144 A | 6/1997 | Hendrickson et al. |
| 5,714,060 A | 2/1998 | Kenley et al. |
| 5,983,947 A | 11/1999 | Utterberg |
| 6,277,277 B1 | 8/2001 | Jacobi et al. |
| 6,308,721 B1 | 10/2001 | Bock et al. |
| 6,325,775 B1 | 12/2001 | Thom et al. |

FOREIGN PATENT DOCUMENTS

| | | |
|---|---|---|
| DE | 2907832 | 4/1980 |
| EP | 0 134 436 B1 | 3/1985 |
| EP | 0 256 956 B1 | 2/1988 |
| EP | 0 282 539 B1 | 9/1988 |
| EP | 0 116 596 B1 | 11/1990 |
| EP | 0 611 227 A1 | 8/1994 |
| EP | 0 643 808 B1 | 3/1995 |
| EP | 0 679 099 B1 | 11/1995 |
| EP | 0 686 237 B1 | 12/1995 |
| EP | 0 694 125 B1 | 1/1996 |
| EP | 0 695 397 B1 | 2/1996 |
| EP | 0 852 953 B1 | 7/1998 |
| EP | 0 887 100 A1 | 12/1998 |
| EP | 0 893 603 A2 | 1/1999 |
| EP | 0 992 256 A2 | 4/2000 |
| GB | 2067075 A | 7/1981 |
| GB | 2 076 476 A1 | 12/1981 |
| GB | 2 110 564 A | 6/1983 |
| GB | 2 208 896 A | 4/1989 |
| WO | WO 88/01895 | 3/1988 |
| WO | WO 95/13837 | 5/1995 |
| WO | WO 95/17597 | 6/1995 |
| WO | WO 95/17598 | 6/1995 |
| WO | WO 95/17599 | 6/1995 |
| WO | WO 95/17600 | 6/1995 |
| WO | WO 95/17601 | 6/1995 |
| WO | WO 95/17602 | 6/1995 |
| WO | WO 95/17603 | 6/1995 |
| WO | WO 95/17604 | 6/1995 |
| WO | WO 97/02056 | 1/1997 |
| WO | WO 97/10436 | 3/1997 |
| WO | WO 98/22163 | 5/1998 |
| WO | WO 99/13926 | 3/1999 |
| WO | WO 01/08722 | 2/2001 |
| WO | WO 01/08772 A2 | 2/2001 |
| WO | WO 02/26288 A2 | 4/2002 |

INTEGRATED MODULE FOR BLOOD TREATMENT

This is a division of application Ser. No. 10/771,536, filed Feb. 5, 2004, now U.S. Pat. No. 7,223,338, which claims the benefit of priority of Italian Patent Application No. MI2003A000214, filed on Feb. 7, 2003, and claims the benefit of U.S. Provisional Application No. 60/470,451, filed May 15, 2003, the contents of which are incorporated herein by reference.

BACKGROUND OF THE INVENTION

The invention relates to a support element, to an integrated module for blood treatment comprising the support element, and to an apparatus for extracorporeal treatment of blood equipped with the integrated module. The invention also relates to a manufacturing process for an integrated module for blood treatment.

As is known, for carrying out extracorporeal blood treatments, such as, for example, hemodialysis, hemofiltration, hemodiafiltration, plasmapheresis, extracorporeal blood oxygenation, extracorporeal blood filtration or other treatments, there must be present at least one extracorporeal circuit through which the blood is made to circulate in order to be transported towards a treatment device. The treated blood is then returned to the patient's cardiovascular system.

With reference, by way of example, to a dialysis treatment, the extracorporeal circuit used comprises: a dialysis filter constituted by a container body including at least a first and a second chamber, separated from each other by a semipermeable membrane, a blood withdrawal line leading to the first chamber of the dialyzer filter and a blood return line destined to receive blood outletting from the first chamber and to return it to the patient. The second chamber of the dialyzer filter is connected to a dialysis liquid circulation circuit destined to receive the impurities present in the blood, as well as the excess fluid which is to be removed from the patient's blood.

At present, in extracorporeal blood treatment apparatus, the totality of lines destined for dialysis liquid circulation is housed inside the dialysis machine, while the lines forming the extracorporeal blood circuit are changed after each single treatment and are connected to the dialyzer filter, which can be changed either at each treatment or periodically, according to needs.

From the structural point of view, the dialyzer filter, the dialysis liquid circulation lines and the lines forming the patient's blood withdrawal and return branches are constituted by separate parts which are connected up and cooperate operatively following assembly.

The market offers apparatus, in particular destined for intensive kidney failure treatment, which are advantageously provided with integrated modules comprising a support structure, a dialyzer filter constrained to the support structure by means of a support element emerging from the support structure, as well as a hydraulic circuit comprising the tubing necessary for defining the withdrawal branch and the return branch of the blood from and to the patient, the lines (if present) for infusion of anticoagulant, or of substitution liquids, the dialysis liquid supply line, the discharge line for discharge liquid outletting from the dialysis filter second chamber.

The above-described integrated modules enable an easy and immediate attachment of the lines on the treatment apparatus and do not need any connection between the treatment device, for example a dialyzer filter, and the various tubes or lines destined to carry blood and other fluids. Further, the integrated modules enable removal both of the tubes carrying the blood and those carrying other fluids once the treatment has been concluded. In other words, with a simple loading operation and a connecting-up of the terminals and the fluid transport lines to the relative sources, i.e. bags or other, the user can start up the dialysis apparatus.

Similarly, once the treatment has been concluded, a small number of disconnecting operations and dismounting of the integrated module from the blood treatment machine will enable the operator to completely remove the extracorporeal circuit, the blood treatment device, any tubing for circulation of infusion liquids as well as for the dialysis liquid.

The ease with which the module can be set up guarantees efficiency and speed, much to be appreciated in the case of intensive treatment, where the personnel involved, not necessarily expert in the use of blood treatment machines, can operate quickly and extremely reliably.

Though the above-described integrated modules have had a notable market success, they have shown themselves to be susceptible to improvement in various aspects.

Firstly, in the prior art, the connection between the support body and the blood treatment device includes an additional support interpositioned between the body of the treatment device and the support element, considerably complicating the overall structure of the integrated model.

The presence of an intermediate support structure between the support body and the dialyzer body causes the integrated module to be considerably unwieldy.

Additionally, the need to connect the dialyzer filter or another treatment device used with the extracorporeal blood circuit lines and the treatment fluid lines constitutes a further difficulty, as the connecting-up operations have to be performed in a zone which is difficult to access.

The above has obviously hampered the possibility of automating the assembly stages, considerably increasing production costs of the integrated modules at present on the market.

SUMMARY OF THE INVENTION

A main aim of the present invention is to make available a support element for an integrated module for blood treatment, and an integrated module for blood treatment comprising the support element, which overcome all of the above-described limitations and drawbacks.

In particular, an aim of the present invention is to provide a new support element which is easily and automatically assemblable with a blood treatment device, consequently reducing the overall costs for realization of an integrated module for extracorporeal blood treatment.

These aims and more besides will better emerge from the detailed description that follows, of a support element and an integrated module for blood treatment, comprising the support element as characterized in one or more of the appended claims.

Further characteristics and advantages will better emerge from the detailed description that follows of some preferred embodiments of a support element and an integrated module incorporating the support element of the present invention.

The following detailed description will also illustrate a manufacturing process of an integrated module for blood treatment, according to the invention.

BRIEF DESCRIPTION OF THE DRAWINGS

The detailed description will now be made with reference to the accompanying figures of the drawings, provided as a non-limiting example, in which.

DETAILED DESCRIPTION

Figure 1:
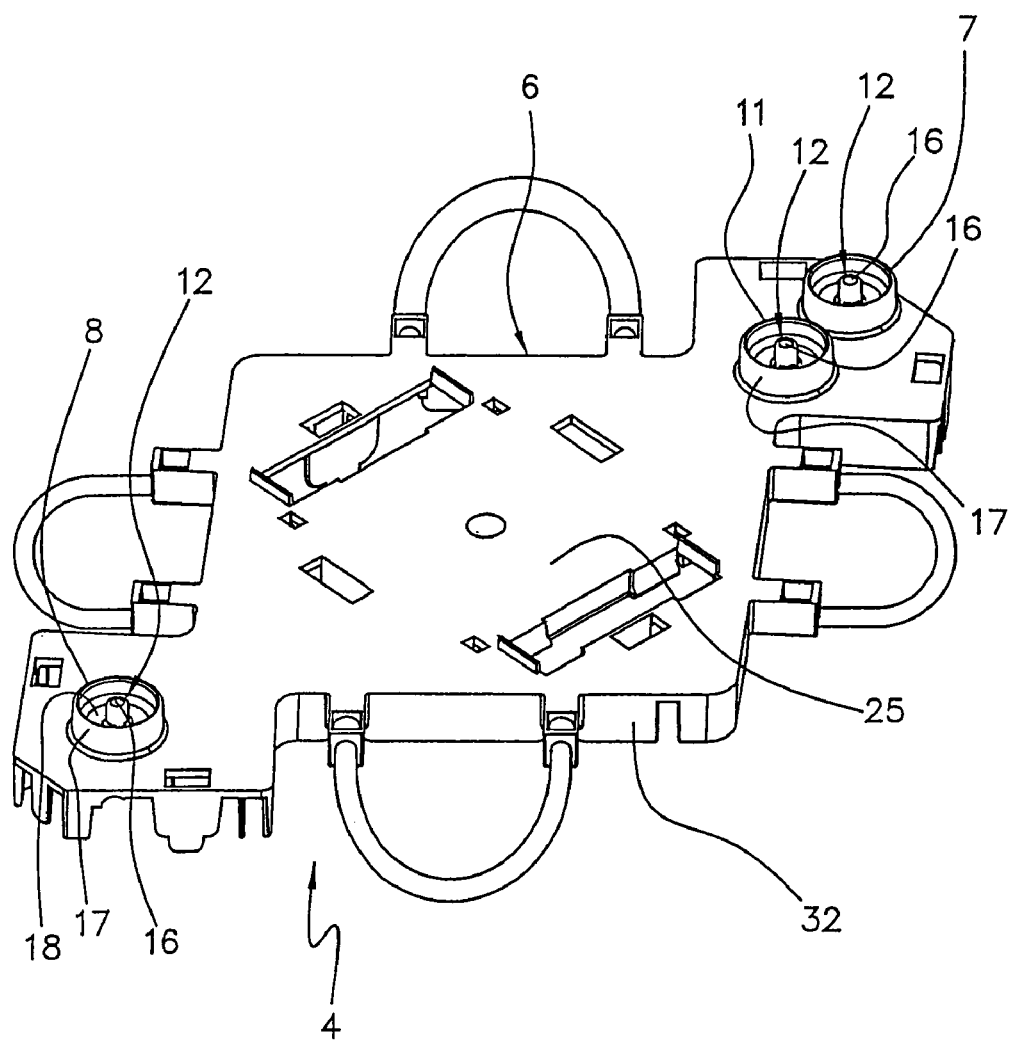
FIG. 1 is a perspective view of a support element for an integrated module according to a first embodiment of the invention.

With reference to the accompanying figures of the drawings, 1 denotes in its entirety an integrated module for blood treatment in accordance with the present invention. The module 1 can be engaged to a machine for extracorporeal blood treatment 2, provided with one or more pumps 3 destined to cooperate with the module 1. The module 1 comprises a support element 4 to which a blood treatment device 5, for example a plasma-filter, a hemodialysis filter, a hemofiltration filter, a filter for hemodiafiltration or a different unit.

In greater detail, the support element 4 comprises a base body 6 exhibiting at least a first and at least a second connector 7 and 8, distanced one from another, destined to receive and connect with corresponding counter-connectors 9 and 10 of the blood treatment device 5. The first and second connectors 7 and 8 are directly constrained to the base body 6; in the illustrated embodiments the connectors 7 and 8 are made of a rigid plastic material and in a single piece with the base body 6.

The support element 4 exhibits a third connector 11, distanced from the connectors 7, 8 and directly constrained on the base body 6; in the illustrated embodiments the third connector 11 is made of rigid plastic material and in a single piece with the base body 6; the three connectors define pairs of connectors having differentiated interaxes for engaging with corresponding pairs of counter-connectors associated to different blood treatment devices which are mountable on the support element 4. This is so that a single base body 6 can be used to realize integrated modules having different characteristics, thanks to the possibility of engaging treatment devices 5 which are not only different as regards the membrane, but also in terms of overall size and therefore interaxes of the relative counter-connectors.

Each of the connectors 7, 8, 11 constitutes a rigid support and defines a fluid passage having a first end portion 12, destined to be placed in fluid communication with a corresponding channel 13 present in a respective counter-connector 9, 10 exhibited by the blood treatment device 5; each connector 7, 8, 11 also exhibits a second end portion 14, destined to be placed in fluid communication with a fluid distribution circuitry 15 associable to the base body 6. In a further structural detail, each of the connectors 7, 8, 11 comprises a tubular channel 16, defining the first end portion 12, a sealing collar 17, in a position which is radially external to the tubular channel 16, and a connecting wall 18, which develops continuously between an external lateral surface 19 of the tubular channel 16 and an internal lateral surface 20 of the sealing collar 17.

The external lateral surface 19 of the tubular channel 16, the internal lateral surface 20 of the sealing collar 17 and the connecting wall 18 together define an annular seating 21, a bottom of which is delimited by the connecting wall 18, shaped in order to receive and engage a corresponding counter-connector of the blood treatment device.

The tubular channel 16 is coaxially arranged with respect to the sealing collar 17, and has geometry of revolution therewith, with a common axis of symmetry. The annular seating 21 exhibits an increasing radial dimension as it progresses from the bottom connecting wall 18; it comprises a first zone 22, adjacent to the bottom and having a constant radial dimension; a second zone 23, distal with respect to the bottom and having a constant radial dimension which is greater than the radial dimension of the first zone 22; and a third zone 24, which is a transit zone between the first and second zones 22 and 23 and which has a progressively growing radial dimension as it progresses away from the bottom connecting wall 18.

The tubular channel 16 and the sealing collar 17 of each connector 7, 8, 11 are parallel to one another in the base body 6, defining a single coupling direction with the corresponding counter-connectors of a treatment device 5.

In the illustrated embodiments, the various counter-connectors and connectors exhibit axes of symmetry which are perpendicular to a frontal wall 25 of the support element 4.

The support element 4 shown in FIGS. 4-7 further comprises a fourth connector 26 which is distanced from the first, second and third connectors 7, 8 and 11. The fourth connector 26 is also directly connected to the support element 4.

In the embodiment of FIGS. 4-7 the fourth connector 26 is made of rigid plastic in a single piece with the base body 6 and defines, with at least one of the other connectors 7, 8 and 11 a further pair of connectors which can be engaged to a corresponding pair of counter-connectors associated to a blood treatment device mountable to the support element 4.

The fourth connector 26 comprises a central cylindrical body 27 for positioning, a sealing collar 28 located in a radially external position with respect to the central cylindrical body 27, and a bottom connecting wall 29 which develops continuously between an external lateral surface 30 of the central cylindrical body 27 and an internal lateral surface 31 of the collar 28. The fourth connector 26 defines a connecting and sealing site for a counter-connector of the blood treatment device 5.

Figure 6:
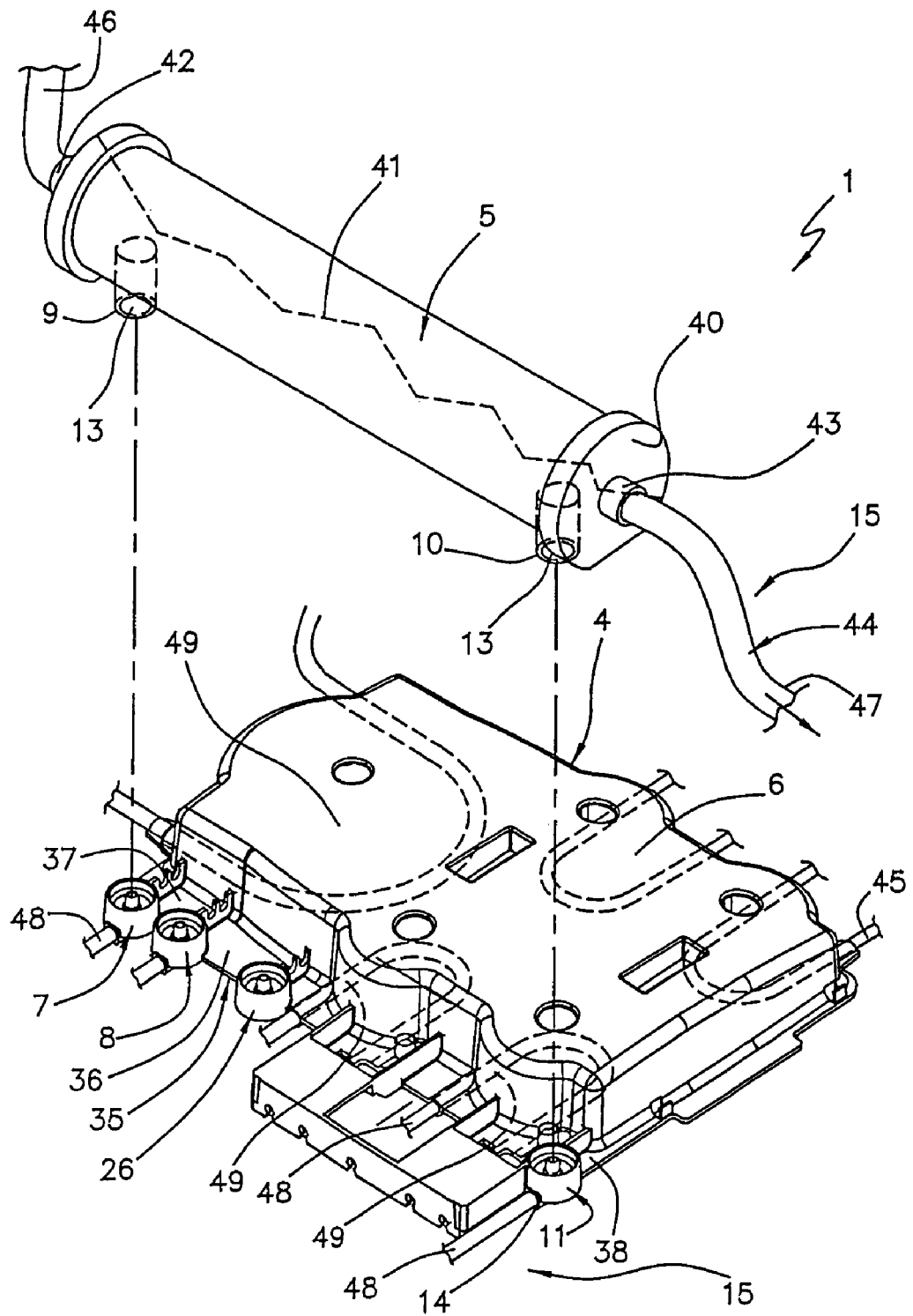
FIG. 6 is a perspective view of an integrated module for extracorporeal treatment of blood with the support element of FIG.5.
Figure 7A:
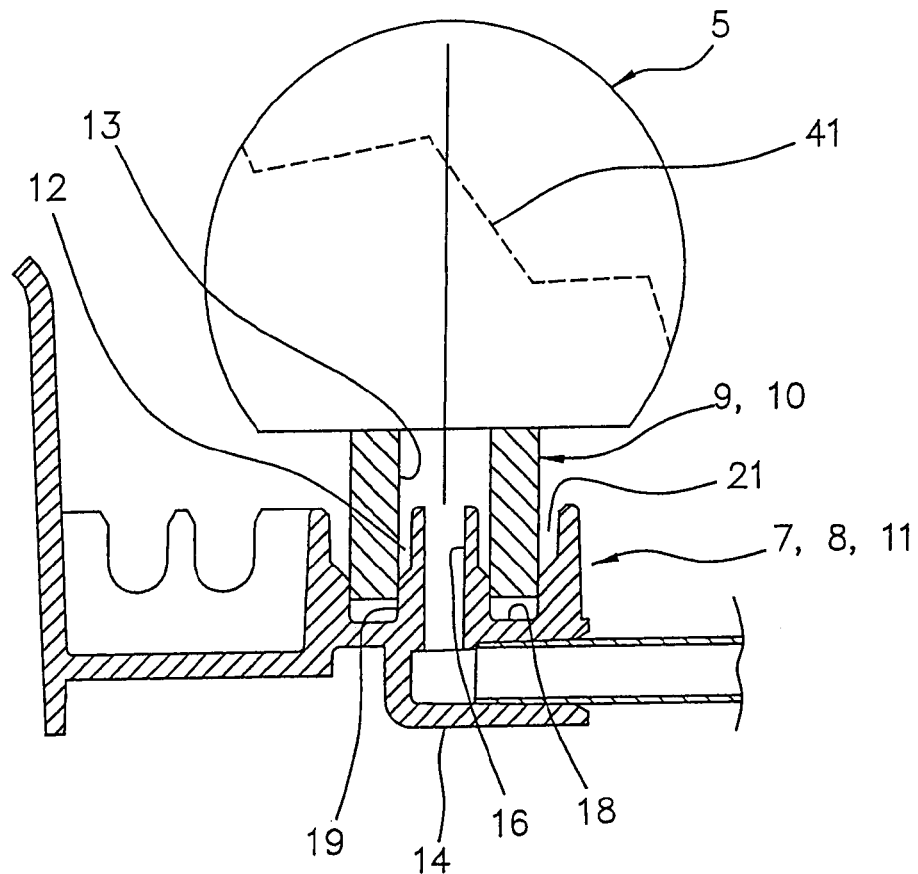
FIG. 7a shows a detail of the module of FIG. 6, relating to a coupling between a seating of the support element and a corresponding connector of a blood treatment device.
Figure 7B:
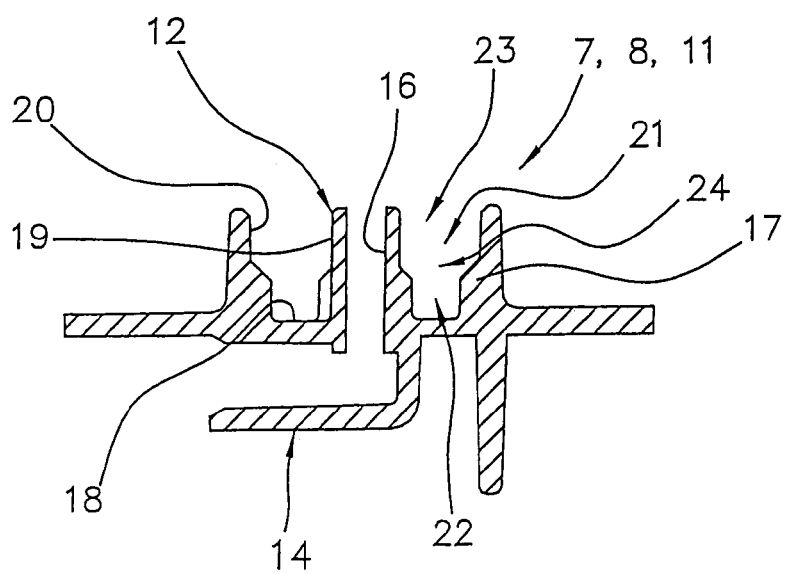
FIG. 7b shows a detail of FIG. 1.
Figure 8:
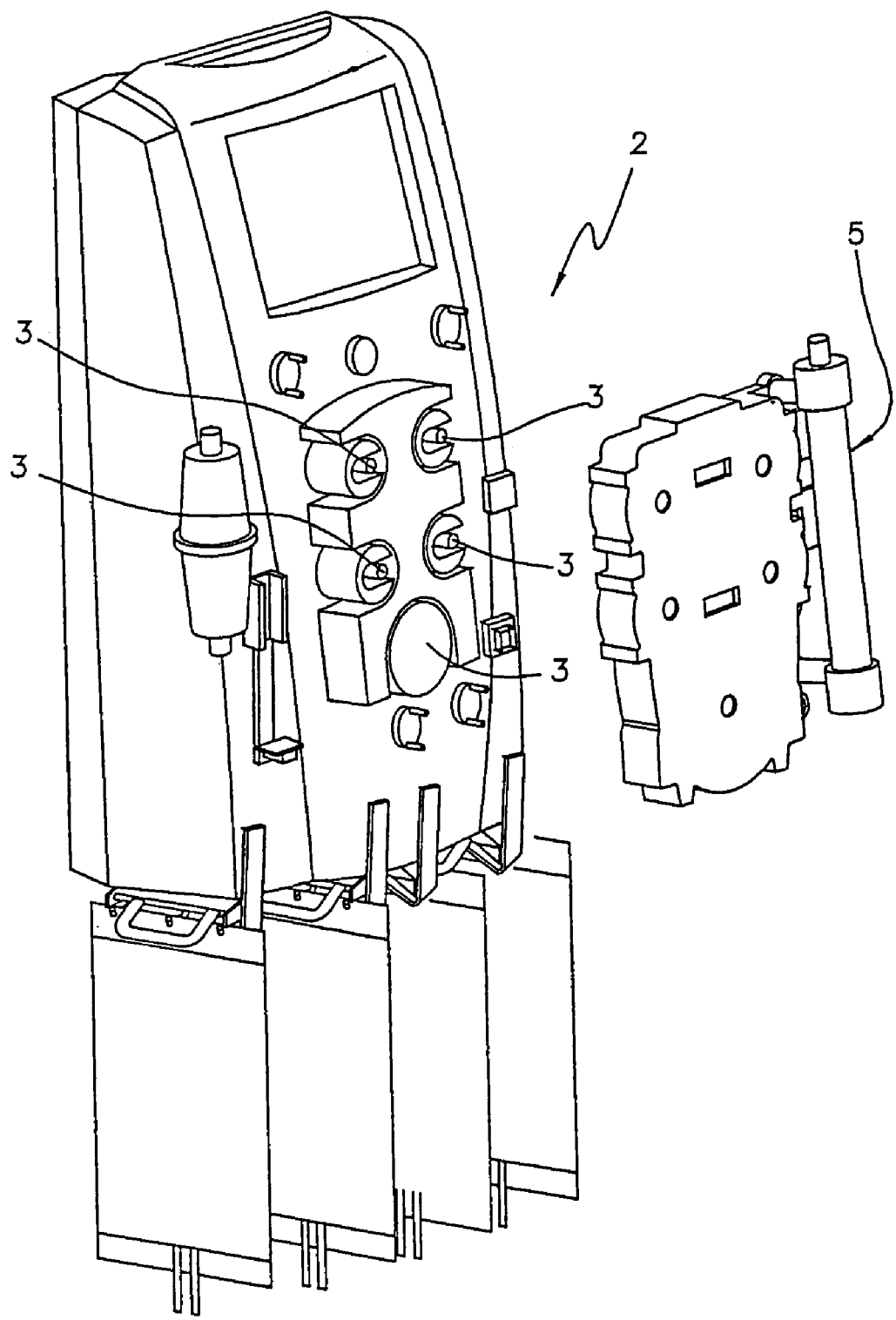
FIG. 8 schematically illustrates the module of FIG. 6 constrained on a frontal operative wall of a machine for extracorporeal blood treatment.

As shown in FIGS. 6, 7a (and the same goes for the support elements of FIGS. 1-3, 7b), the various connectors are made of rigid material in order to offer a mechanical support to the blood treatment device and, according to each individual case, to define a passage or an obstruction for fluid passing through the counter-connectors 9, 10.

Figure 4:
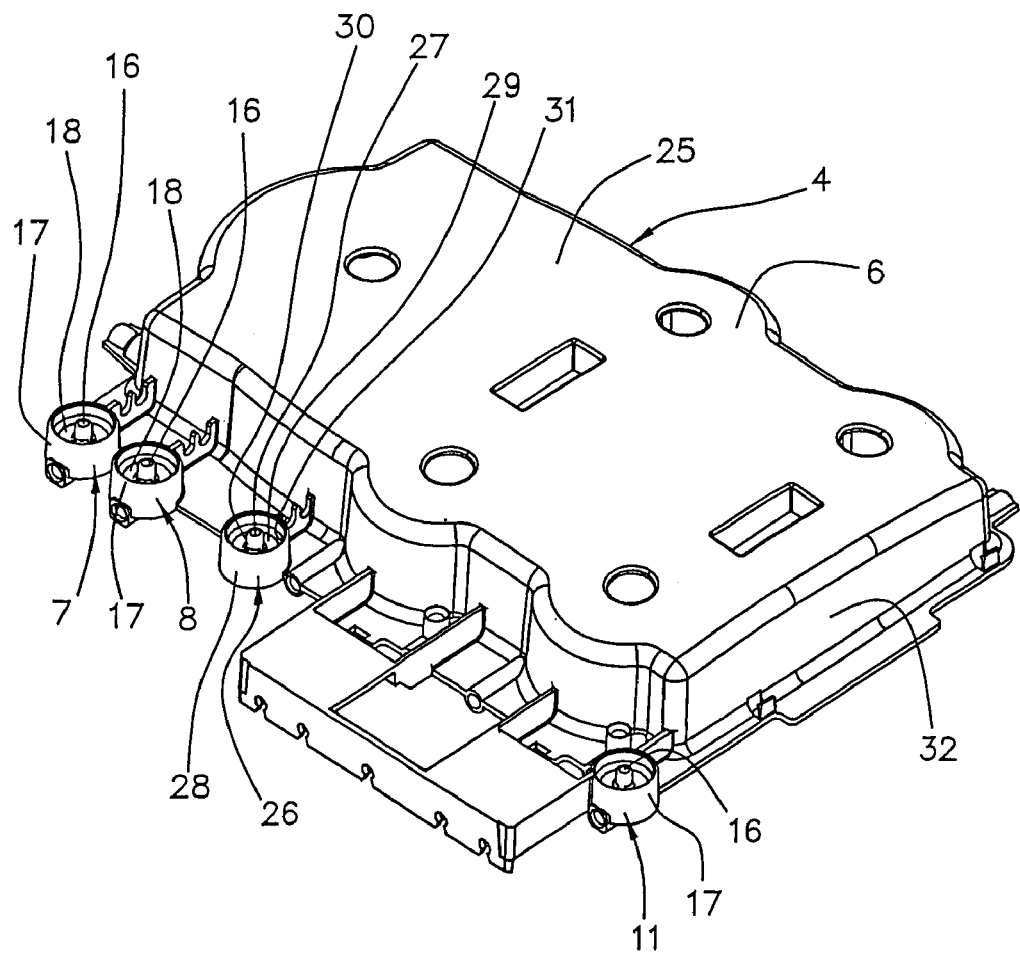
FIG. 4 is a perspective view of a support element for an integrated module in a second embodiment of the invention.
Figure 5:
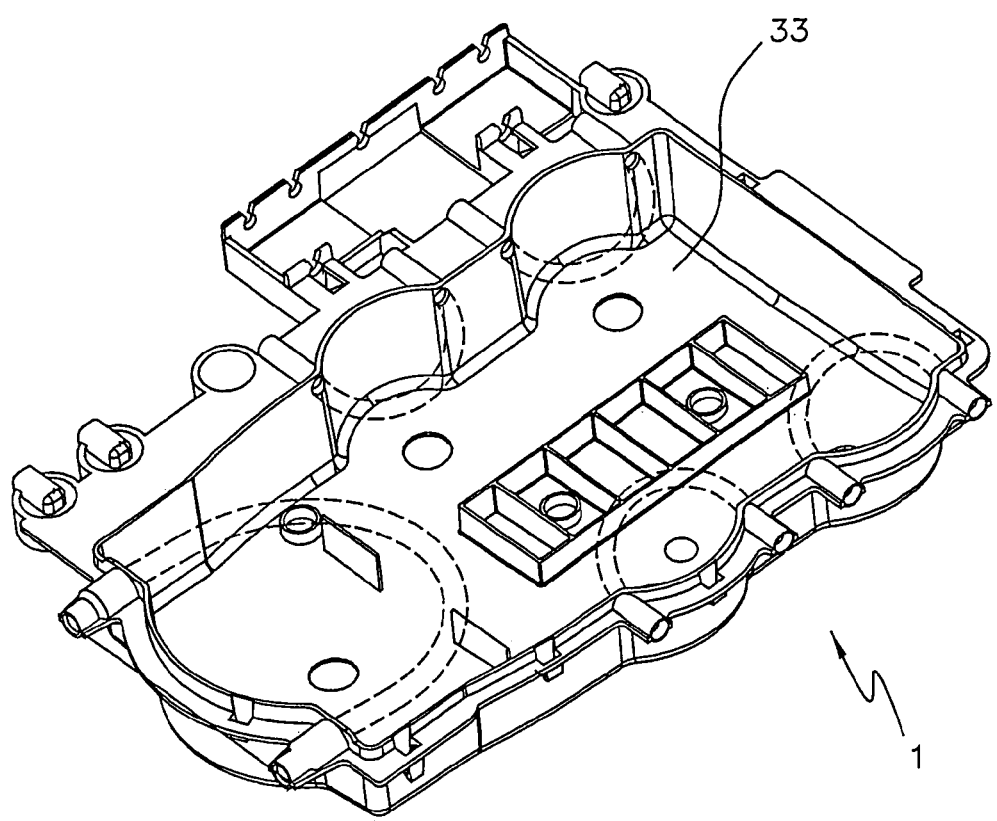
FIG. 5 shows the support element of FIG. 4 in an upturned position relative to the position of FIG. 4.

In the support element of FIGS. 4-6 the four connectors are aligned and arranged on one side of the base body 6. More precisely, the base body 6 of the element illustrated in FIGS. 4-6 and 7a comprises a frontal wall 25 and a perimeter wall 32 connected around an edge thereof to the frontal wall 25, which together define a works housing area 33 which can house at least a portion of the works of the support element, i.e. a fluid distribution circuitry 15 destined to be associated to the support element 4.

The works housing area 33 exhibits an open side 34 which enables the integrated module 1 to be correctly positioned and adequately locked onto the machine, as will be better described herein below.

The support element 4 exhibits an auxiliary structure 35 which extends laterally and externally with respect to the works housing area 33 from a base zone 36 of the perimeter wall 32. The four connectors emerge from the auxiliary structure 35: the first, second and fourth connector 7, 8, 26 are adjacently situated, and arranged at a first end zone 37 of the auxiliary structure 35, while the third connector 11 is located at a second end zone 38, opposite the first end zone 37.

Figure 2:
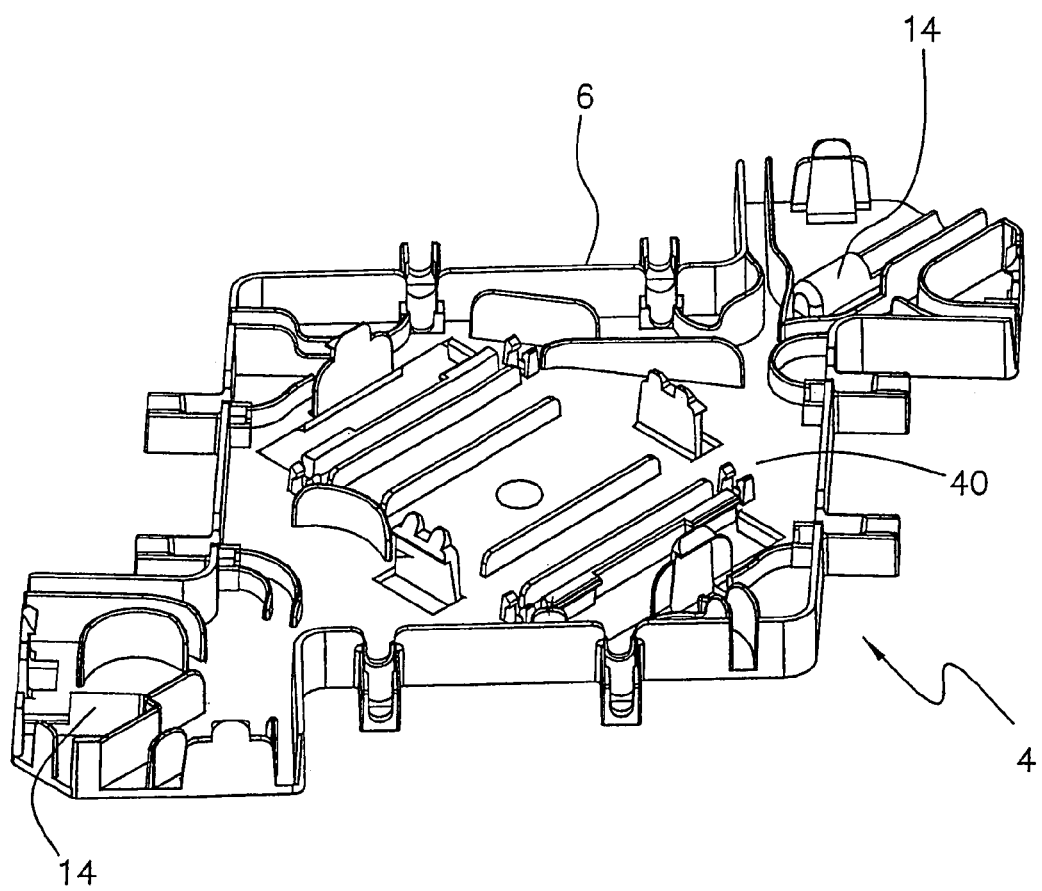
FIG. 2 shows the support element of FIG. 1 in an upturned position relative to the position of FIG. 1.
Figure 3:
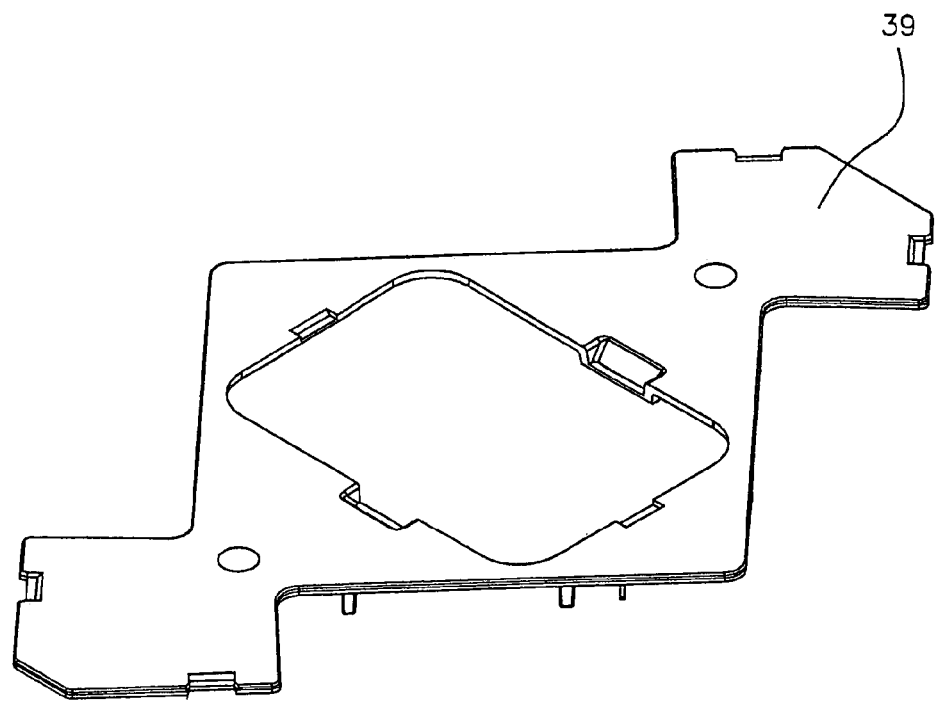
FIG. 3 is a perspective view of a cover for closing an open side of the support element of FIG. 1.

In the illustrated embodiment of FIGS. 1-3, the base body 6 comprises a frontal wall 25 and a perimeter wall 32 joined at an edge thereof to the frontal wall 25, defining a works housing area 33 which can house at least a portion of the fluid distribution circuitry 15 destined to be associated to the support element 4.

In this embodiment, however, the connectors 7, 8 and 11 are not aligned and emerge directly from the frontal wall 25. Further, a cover 39 is associated to the perimeter wall 32 on an opposite edge thereof with respect to the frontal wall 25.

A support element according to the invention can advantageously be used for realizing an integrated module, such as for example the module illustrated in FIG. 6, where by way of example the support element 4 of FIGS. 4 and 5 is used.

As can be observed, the blood treatment device 5 is fixed to the support element 4 by at least one pair of connectors; the blood treatment device comprises a body 40, at least one semipermeable membrane 41 (for example a parallel hollow fiber membrane or a plate membrane) operating internally of the body 40 and defining a first chamber and a second chamber; a first and a second connector are associated to the body 40 and fixed to the respective connectors on the base body 6.

The first and second counter-connectors 9, 10, are tubular and are in fluid communication with the second chamber of the treatment device and with respective first end portions 12 of the connectors.

The treatment device exhibits an inlet port 42 to the first chamber, and at least one outlet port 43 from the first chamber, for connection of an extracorporeal blood circuit line 44 or another physiological fluid.

A fluid distribution circuitry 15 is attached to the support element 4 and cooperates with the treatment device 5. In more detail, the circuitry comprises:

- at least one discharge line 45 of discharge fluid, in communication with the second terminal portion 14 of one of the connectors;
- at least one blood line 44 having a blood withdrawal branch 46, placed in communication with the inlet 42 of the first chamber, and at least one branch 47 of a blood return line, placed in communication with the outlet 43 of the first chamber;
- at least one supply line 48 of fresh dialysis liquid, placed in communication with the second end portion 14 of another of the connectors.

Each of the lines is constrained to the support element 4, defining at least one tract of tubing 49 which is arranged in a U-shape, in relation to the support element 4.

During operation the U-shaped tracts are destined to cooperate with the respective peristaltic pumps 3 located on a panel of a machine for extracorporeal blood treatment. Each tract of U-shaped tubing extends internally or externally (FIG. 7) with respect to the perimeter wall 32 of the support element 4.

Figure 9:
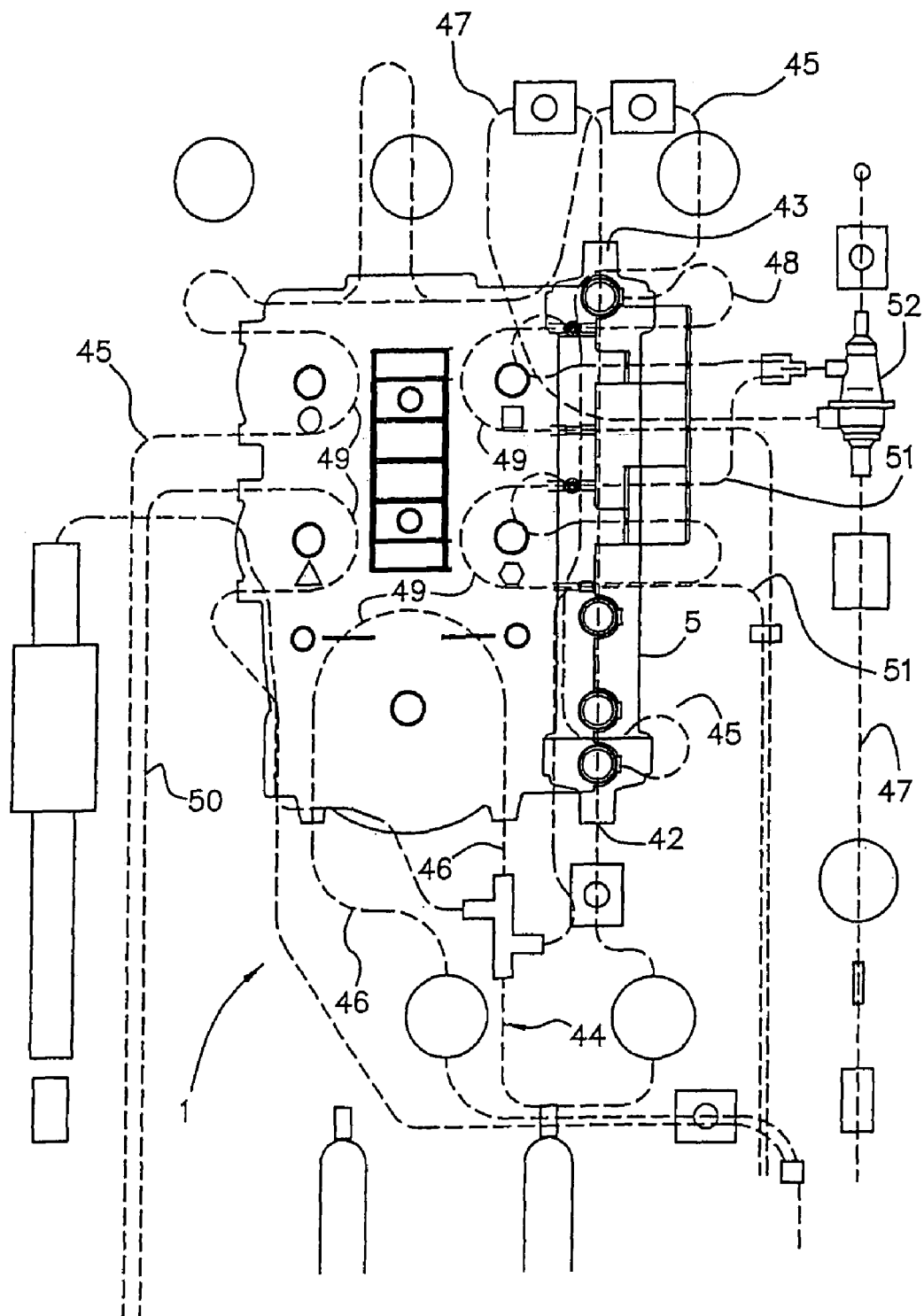
FIG. 9 is a schematic representation of the module of FIG. 6 in CRRT (continuous renal replacement therapy) configuration.

FIG. 9 is a diagram of the integrated module 1 in the CRRT configuration. As can be observed, the module 1 also has lines 50 and 51 for respective pre and post blood pump infusions (pre-dilution and/or post-dilution).

An air separator device 52 operates on the branch 47 of the blood line 44 and receives an infusion line 51.

The invention also relates to an assembly procedure for an integrated module for fluid treatment which comprises the stages of predisposing a support element 4, for example such as in FIGS. 1-3 or in FIGS. 4-6, as well as a treatment device 5 which is intended for coupling to the support element 4. The blood treatment device 5 is then fixed to the support element 4. Finally a fluid distribution circuitry 15 is associated to the support element 4 and to the blood treatment device 5 so as to create the necessary blood circulation lines, the discharge lines, the infusion lines for any liquid substitution lines, and dialysis lines.

The connection of the distribution circuitry to the blood treatment device can be done before, at the same time as or after the circuitry fixing stage to the support element 4.

The fixing stage of the blood treatment device to the support element 4 comprises the sub-stages of selecting a pair of connectors to which the counter-connectors 9, 10 on the blood treatment device are to be connected, applying a predetermined quantity of glue, normally polymer-resin based, in the annular seatings 21 of each chosen connector, at least partially inserting each counter-connector in the respective annular seating in order to obtain a mechanical bond and a liquid-proof seal coupling.

During the insertion stage, at least a portion of the glue applied in the annular seating actually settles in the second zone 23 of the annular seating. On completion of the counter-connector insertion stage in the annular seating, the volume of the quantity of glue previously applied added to the volume of the portion of counter-connector housed in the annular seating is less than the overall volume of the annular seating. This prevents any glue material from migrating towards the tubular channel 16 and causing a partial or total occlusion.

The stage of associating a fluid distribution circuitry 15 to the support element 4 and the blood treatment device 5 comprises the sub-stages of liquid-proof sealing of an end portion of a discharge fluid discharge line 45 with the second end portion 14 of one of the connectors, and of sealedly fixing an end portion of a fresh dialysis liquid supply line 48 to the second end portion of a further of the connectors.

The stage of associating the blood distribution circuitry also includes sealedly fixing an end portion of a blood withdrawal branch 46 to an inlet port of the first chamber, and an end portion of a blood return branch 47 to an outlet port of the first chamber.

The fixing of the various above-mentioned end portions can be achieved by gluing, friction fitting or hot-coupling.

The invention provides important advantages.

Firstly, the direct fixing of the blood treatment device to the selected connectors of the support element does not require the use of other support elements of the same device.

Further, the connectors receive on one side the counter-connectors of the blood treatment device and on the other side the end portions of distribution circuitry lines, realizing a contemporaneous mechanical and hydraulic connection between the fluid distribution circuitry and the blood treatment device.

The presence of various connectors means the treatment device can be used with connectors having different inter-axes.

The special fixing modality of the blood treatment device and the various fluid lines to the support element considerably facilitates the assembly process of an integrated module according to the invention.

The specific structure of the integrated module and the support element minimizes the length of fluid line needed to realize the connections with the blood treatment device.

The invention claimed is:

1. An integrated module for fluid treatment, comprising:
   a support element having:
   a base body;
   at least a first and at a least a second connector associated with the base body and distanced one from another;
   at least an intermediate connector interposed between said first and second connectors, distanced from said first connector and from said second connector and directly constrained to the base body, said first, second, and intermediate connectors defining pairs of connectors having differentiated interaxes there-between for engaging to corresponding pairs of counter-connectors associated with various blood treatment devices which are mountable on the support element;
   at least one blood treatment device engaged on the support element and having:
   a containment body presenting a main development axis and including a lateral surface and first and second end surfaces;
   at least one semi-permeable membrane operating internally of the containment body and defining a first chamber and a second chamber;
   a first counter-connector and a second counter-connector, both emerging from the lateral surface of the containment body and being fixed to a pair of connectors selected from the first, second, and intermediate connectors associated with the base body, at least one of the first counter-connector and the second counter-connector being placed in fluid communication with the second chamber of the blood treatment device and with respective first end portions of said pair of connectors, wherein the intermediate connector is not connected to a counter-connector of the blood treatment device;
   at least one inlet port to the first chamber associated with the first end surface and emerging axially along the development axis; and
   at least one outlet port from the first chamber associated with the second end surface and emerging axially along the development axis;
   a fluid distribution circuitry associated with the support element and cooperating with the blood treatment device, each of said pair of connectors presenting a fluid passage having a first end portion in fluid communication with a corresponding channel in a respective counter-connector on the blood treatment device and a second end portion in fluid communication with the fluid distribution circuitry the fluid distribution circuitry presenting at least one blood line having a blood withdrawal branch placed in fluid communication with the inlet port of the first chamber and emerging axially from the first end surface along the development axis and at least one blood return branch placed in fluid communication with the outlet port of the first chamber and emerging axially from the second end surface along the development axis.

2. The integrated module of claim 1, wherein the pair of second connectors are directly constrained to the base body.

3. The integrated module of claim 2, wherein the pair of connectors are made in a single piece with the base body.

4. The integrated module of claim 1, wherein the intermediate connector is made in a single piece with the base body.

5. The integrated module of claim 1, wherein each of said pair of connectors comprises:
   a tubular channel defining said first end portion;
   a sealing collar set in a radially external position with respect to the tubular channel; and
   a connecting wall developing continuously between an external lateral surface of said tubular channel and an internal lateral surface of said sealing collar to define an annular seating for engagement of each counter-connector.

6. The integrated module of claim 5, wherein the tubular channel defining said first end portion is coaxially arranged with respect to the sealing collar, said annular seating exhibiting a bottom delimited by said connecting wall.

7. The integrated module of claim 6, wherein said annular seating exhibits a radial dimension that increases progressively in a direction moving away from a bottom wall.

8. The integrated module of claim 7, wherein said annular seating exhibits:
   a first zone, adjacent to said bottom wall and having a constant radial dimension;
   a second zone, distal of said bottom wall and having a constant radial dimension greater than the radial dimension of the first zone; and
   a third transition zone configured between the first zone and the second zone, said third transition zone having a progressively increasing dimension in a distancing direction from said bottom wall.

9. The integrated module of claim 5, wherein the tubular channel and the sealing collar of each connector are parallel to one another as they emerge from the base body, defining a single coupling direction for coupling with corresponding counter-connectors of a blood treatment device.

10. The integrated module of claim 1, comprising a fourth connector, distanced from said first, second, and intermediate connectors, said fourth connector being made as a single piece with the base body and defining, with at least one of said first, second, and intermediate connectors, a further pair of connectors which can be engaged to a corresponding pair of counter-connectors associated with a blood treatment device which is mountable on the support element.

11. The integrated module of claim 10, wherein the fourth connector comprises:
   a central cylindrical positioning body;
   a sealing collar, set in a radially external position to the cylindrical positioning body; and
   a connecting wall, developing continuously between an external lateral surface of said cylindrical positioning body and an internal lateral surface of said cylindrical positioning body and an internal lateral surface of said sealing collar;
   said fourth connector defining a connecting and sealing site for a counter-connector of the blood treatment device.

12. The integrated module of claim 2, wherein said pair of connectors and said base body are made of a rigid material in order to offer a mechanical support for the blood treatment device.

13. The integrated module of claim 1, wherein said first, second, and intermediate connectors are aligned one next to another.

14. The integrated module of claim 2, wherein said pair of connectors are arranged on a side of the base body.

15. The integrated module of claim 1, wherein said base body comprises a frontal wall and a perimeter wall, which perimeter wall is connected by a side thereof to the frontal wall and defines a works area within which at least a portion of a fluid distribution circuitry configured to be associated with the support element can be housed.

16. The integrated module of claim 15, comprising an auxiliary structure extending laterally and externally with respect to said works area from a base zone of the perimeter wall, said pair of connectors emerging from said auxiliary structure.

17. The integrated module of claim 1, wherein said first, second, and intermediate connectors are not aligned one next to another.

18. The integrated module of claim 1, wherein the base body comprises a frontal wall, from which said pair of connectors directly project, and a cover associated with a perimeter wall at an opposite edge thereof with respect to the frontal wall.

19. The integrated module of claim 1, wherein said blood treatment device is fixed to the base body by at least the pair of said connectors.

20. The integrated module of claim 19, wherein said pair of connectors is interpositioned between the counter-connectors and a portion of the fluid distribution circuitry.

21. The integrated module of claim 1, wherein the fluid distribution circuitry comprises at least one discharge line of a discharge fluid in communication with the second end portion of one of said pair of connectors.

22. The integrated module of claim 21, wherein the fluid distribution circuitry comprises at least one fresh dialysis liquid supply line in communication with the second end portion of another of said pair of connectors.

23. The integrated module of claim 22, wherein the fluid distribution circuitry comprises at least one blood circuit line having a blood withdrawal branch in communication with the inlet port of the first chamber, and at least one blood return branch in communication with the outlet port of the first chamber.

24. The integrated module of claim 21, wherein at least one of said at least one distribution lines is constrained to the support element and defines at least one tract of tubing configured in a U-shape in relation to the support element, said at least one tract of tubing being destined during operation to cooperate with a peristaltic pump.

25. The integrated module of claim 24, wherein the at least one tract of tubing configured in a U-shape extends internally or externally with respect to the perimeter wall of the support element.

26. The integrated module of claim 1, wherein the counter-connectors of the blood treatment device are fixed to the pair of said connectors by a prefixed quantity of glue in the annular seatings of each of said connectors, each of said counter-connectors being partially inserted into a respective annular seating in order to obtain a mechanical lock and a liquid-proof seal.

27. The integrated module of claim 26, wherein at least a portion of the prefixed quantity of glue is configured in a second zone of the respective annular seating, and wherein a volume of said prefixed quantity of glue, added to a volume of a portion of each counter-connector housed in the annular seating, is less than a total volume of the annular seating.

28. The integrated module of claim 23, wherein the end portion of the discharge line is liquid-proof fixed to the second end portion of one of said connectors, the end portion of the fresh dialysis liquid supply line is liquid-proof fixed to the second end portion of another of said connectors, the end portion of the blood withdrawal branch is liquid-proof fixed to the inlet port of the first chamber, and the end portion of the blood return branch is liquid-proof fixed to the outlet port of the first chamber.

29. An integrated module for fluid treatment, comprising:
a support element having:
a base body;
a first and a second connector associated with the base body and distanced one from another;
at least an intermediate connector interposed between said first and second connectors, distanced from said first connector and from said second connector and directly constrained to the base body, said first and said second connectors being the outermost connectors, said first, second, and intermediate connectors defining pairs of connectors having differentiated interaxes there-between for engaging to corresponding pairs of counter-connectors associated with various blood treatment devices which are mountable on the support element;
at least one blood treatment device engaged on the support element and having:
a containment body presenting a main development axis and including a lateral surface and first and second end surfaces;
at least one semi-permeable membrane operating internally of the containment body and defining a first chamber and a second chamber;
a first counter-connector and a second counter-connector, both emerging from the lateral surface of the containment body and being fixed to a pair of connectors selected from the first, second, and intermediate connectors associated with the base body, at least one of the first counter-connector and the second counter-connector being placed in fluid communication with the second chamber of the blood treatment device and with respective first end portions of said pair of connectors, wherein the remaining connector of the first, second and intermediate connectors is not connected to a counter-connector of the blood treatment device;
at least one inlet port to the first chamber associated with the first end surface and emerging axially along the development axis; and
at least one outlet port from the first chamber associated with the second end surface and emerging axially along the development axis;
a fluid distribution circuitry associated with the support element and cooperating with the blood treatment device, each of said first and second connectors presenting a fluid passage having a first end portion in fluid communication with a corresponding channel in a respective counter-connector on the blood treatment device and a second end portion in fluid communication with the fluid distribution circuitry, the fluid distribution circuit presenting at least one blood line having a blood withdrawal branch placed in fluid communication with the inlet port of the first chamber and emerging axially from the first end surface along the development axis and at least one blood return branch placed in fluid communication with the outlet port of the first chamber and emerging axially from the second end surface along the development axis.

30. An integrated module for fluid treatment, comprising:
a support element having:
a base body;
at least a first and at a least a second connector associated with the base body and
distanced one from another;
at least an intermediate connector, distanced from said first connector and from said second connector, said first, second and intermediate connectors defining pairs of connectors having differentiated interaxes there-between for engaging to corresponding pairs of counter-connectors associated with various blood treatment devices which are mountable on the support element, wherein the first, the second and the intermediate connectors are directly constrained to the base body and the first, the second and the intermediate connectors are made in a single piece with the base body;

at least one blood treatment device engaged on the support element and having:

a containment body presenting a main development axis and including a lateral surface and first and second end surfaces;

at least one semi-permeable membrane operating internally of the containment body and defining a first chamber and a second chamber;

a first counter-connector and a second counter-connector, both emerging from the lateral surface of the containment body and being fixed to a pair of the three connectors associated with the base body, at least one of the first counter-connector and the second counter-connector being placed in fluid communication with the second chamber of the blood treatment device and with respective first end portions of said pair of connectors, wherein the remaining connector of the first, second and intermediate connectors is not connected to a counter-connector of the blood treatment device;

at least one inlet port to the first chamber associated with the first end surface and emerging axially along the development axis; and at least one outlet port from the first chamber associated with the second end surface and emerging axially along the development axis;

a fluid distribution circuitry associated with the support element and cooperating with the blood treatment device, each of said first and second connectors presenting a fluid passage having a first end portion in fluid communication with a corresponding channel in a respective counter-connector on the blood treatment device and a second end portion in fluid communication with the fluid distribution circuitry, the fluid distribution circuit presenting at least one blood line having a blood withdrawal branch placed in fluid communication with the inlet port of the first chamber and emerging axially from the first end surface along the development axis and at least one blood return branch placed in fluid communication with the outlet port of the first chamber and emerging axially from the second end surface along the development axis.

* * * * *